(12) United States Patent
Johnson et al.

(10) Patent No.: US 9,259,750 B2
(45) Date of Patent: Feb. 16, 2016

(54) DEVICES AND METHODS FOR IMPROVED DELIVERY OF VOLATILE LIQUIDS

(75) Inventors: Andrew Johnson, Hull (GB); Loic Marouse, Hull (GB)

(73) Assignee: Reckitt & Colman (Overseas) Limited, Slough, Berkshire (GB)

( * ) Notice: Subject to any disclaimer, the term of this patent is extended or adjusted under 35 U.S.C. 154(b) by 216 days.

(21) Appl. No.: 14/128,069

(22) PCT Filed: Jun. 21, 2012

(86) PCT No.: PCT/GB2012/051441
§ 371 (c)(1),
(2), (4) Date: Feb. 20, 2014

(87) PCT Pub. No.: WO2012/175971
PCT Pub. Date: Dec. 27, 2012

(65) Prior Publication Data
US 2014/0175682 A1    Jun. 26, 2014

(30) Foreign Application Priority Data

Jun. 24, 2011    (GB) .................................. 1110724.0

(51) Int. Cl.
*B01F 3/04*       (2006.01)
*B05B 7/24*       (2006.01)
(Continued)

(52) U.S. Cl.
CPC .............. *B05B 7/2483* (2013.01); *A01M 1/205* (2013.01); *A01M 1/2044* (2013.01); *A61L 9/127* (2013.01);
(Continued)

(58) Field of Classification Search
CPC .... B01F 3/04; B01F 3/04007; B01F 3/04049; B01F 3/04056; B05B 7/2483
USPC ............ 261/76, 78.2, 30, 99, 119.1, DIG. 65, 261/DIG. 75, DIG. 88
See application file for complete search history.

(56) References Cited

U.S. PATENT DOCUMENTS

| | | | |
|---|---|---|---|
| 2,612,432 A | 9/1952 | Boddy | |
| 2,735,512 A * | 2/1956 | Faust | ........................ F16N 7/34 184/55.2 |

(Continued)

FOREIGN PATENT DOCUMENTS

| | | |
|---|---|---|
| EP | 0092359 A3 | 4/1983 |
| EP | 1076014 A3 | 2/2001 |

(Continued)

OTHER PUBLICATIONS

International Preliminary Report on Patentability for PCT/GB2012/051441 dated Dec. 24, 2013.
(Continued)

*Primary Examiner* — Robert A Hopkins
(74) *Attorney, Agent, or Firm* — Norris Mclaughlin & Marcus PA

(57) ABSTRACT

An emanation system is described comprising and emanation device and a replaceable refill of liquid, wherein the refill comprises: a sealed reservoir of a liquid containing one or more active materials wherein the active material comprises at least ona of: a fragrance; an insecticide; a fungicide; a pesticide; a sanitizing material; and/or a pharmaceutical; a porous wick having a length which extends from the interior of the reservoir to the exterior thereof; a reservoir seal having at least one aperture through which the porous wick extends; and a hollow liquid conduit housed within the wick having a length substantially identical to the wick; and wherein tha device comprises: an air pump; a fluid conduit In fluid communication with tha air pump such that, in use, air pumped by the pump will flow through the fluid conduit; a nozzle located at the end of the fluid conduit remote from tha air pump; a elector constriction provided in the fluid conduit adjacent or substantially adjacent the nozzle; a liquid conduit engaging member provided adjacent the ejector constriction and in fluid communication with the fluid conduit at one end thereof, and configured at the other end to, In use, engage the hollow liquid conduit in the refill.

16 Claims, 2 Drawing Sheets

(51) Int. Cl.
  *A61L 9/12* (2006.01)
  *A61L 9/14* (2006.01)
  *A01M 1/20* (2006.01)
  *A61M 11/06* (2006.01)

(52) U.S. Cl.
  CPC ............... *A61L 9/14* (2013.01); *B01F 3/04049* (2013.01); *B01F 3/04056* (2013.01); *A61L 2209/133* (2013.01); *A61L 2209/135* (2013.01); *A61M 11/06* (2013.01); *B05B 7/2491* (2013.01)

(56) References Cited

U.S. PATENT DOCUMENTS

| | | |
|---|---|---|
| 2,814,081 A | 11/1957 | Stevenson |
| 3,796,541 A | 3/1974 | Gentil |
| 3,872,280 A | 3/1975 | Van Dalen |
| 4,166,087 A | 8/1979 | Cline et al. |
| 4,200,229 A | 4/1980 | Spector |
| 4,346,059 A | 8/1982 | Spector |
| 4,370,300 A | 1/1983 | Mori et al. |
| 4,950,457 A | 8/1990 | Weick |
| 2002/0130146 A1 | 9/2002 | Borut et al. |
| 2002/0168301 A1 | 11/2002 | Channer |
| 2005/0178345 A1 | 8/2005 | Crapser |
| 2005/0199742 A1 | 9/2005 | Maat |
| 2006/0022064 A1 | 2/2006 | Triplett et al. |
| 2006/0045359 A1 | 3/2006 | Chen et al. |
| 2006/0175425 A1 | 8/2006 | McGee et al. |
| 2007/0204387 A1 | 9/2007 | Cornelius et al. |
| 2007/0217771 A1 | 9/2007 | Granger et al. |
| 2008/0149665 A1 | 6/2008 | Hafer et al. |
| 2008/0251598 A1 | 10/2008 | Ross |
| 2010/0187324 A1 | 7/2010 | Feygin et al. |
| 2010/0243754 A1 | 9/2010 | Harris |

FOREIGN PATENT DOCUMENTS

| | | |
|---|---|---|
| EP | 1714662 A1 | 10/2006 |
| EP | 1849485 A1 | 10/2007 |
| FR | 2556242 A1 | 6/1985 |
| GB | 2233230 A | 1/1991 |
| GB | 2357973 A | 7/2001 |
| GB | 2480906 A | 12/2011 |
| GB | 2481635 A | 1/2012 |
| WO | 9607484 A1 | 3/1996 |
| WO | 9949904 A1 | 10/1999 |
| WO | 03003826 A3 | 1/2003 |
| WO | 03103387 A3 | 12/2003 |
| WO | 2004002542 A1 | 1/2004 |
| WO | 2004094071 A1 | 11/2004 |
| WO | 2004096299 A1 | 11/2004 |
| WO | 2006004891 A1 | 1/2006 |
| WO | 2006045359 A1 | 5/2006 |
| WO | 2007109504 A3 | 9/2007 |
| WO | 2008034977 A3 | 3/2008 |
| WO | 2011098641 A1 | 8/2011 |
| WO | 2011161462 A1 | 12/2011 |
| WO | 2012001404 A1 | 1/2012 |
| WO | 2012001405 A1 | 1/2012 |
| WO | 2012059771 A1 | 5/2012 |

OTHER PUBLICATIONS

Written Opinion of the International Searching Authority for PCT/GB2012/051441 dated Oct. 10, 2012.

International Search Report for PCT/GB2012/051441 dated Oct. 10, 2012.

* cited by examiner ically actuate the aerosol to cause a dose of the liquid to
DEVICES AND METHODS FOR IMPROVED DELIVERY OF VOLATILE LIQUIDS This is an application filed under 35 USC 371 of PCT/GB2012/051441.

FIELD OF THE INVENTION

The present invention relates to devices and methods for improved airborne delivery of volatile liquids containing one or more active materials wherein the active material comprises at least one of: a fragrance; an insecticide; a fungicide; a pesticide; a sanitising material; and/or a pharmaceutical.

BACKGROUND

Volatile liquids containing one or more active materials wherein the active material comprises at least one of: a fragrance; an insecticide; a fungicide; a pesticide; a sanitising material; and/or a pharmaceutical are delivered within the domestic environment via a variety of mechanisms. Devices are available with heaters disposed therein to increase the rate of emanation from a surface saturated with the liquid, such a surface could be a wick saturated with a fragranced liquid and the heater is located adjacent the wick surface and nearby a chimney to heat the liquid on the wick surface and cause it to more readily evaporate and disseminate into the surrounding environment through the chimney.

Alternatively such volatile liquids can be loaded in an aerosol canister, the canister holds the liquid under pressure and when the canister valve is opened the liquid is forced out. The liquid is provided with a propellant which evaporates inside the canister to maintain an even pressure and, outside the canister, assist with the mechanical break up of the liquid by evaporating rapidly. Suitable propellants include volatile hydrocarbons such as propane, butane or isobutane.

Aerosols generally provide a satisfactory spray performance but since they require manual operation by a user, they are not considered to be particularly convenient for routine use. Automatic aerosol activation devices exist for operation with metered dose aerosols. These devices are operable to periodically actuate the aerosol to cause a dose of the liquid to be sprayed.

Whilst the automation of the device overcomes the problem of manual operation of a canister, the use of aerosols containing such propellants is becoming increasingly less desirable since these volatile hydrocarbons carry the disadvantage of being flammable, the rising cost of oil is rendering them increasingly expensive and they also carry the further disadvantage of being an atmospheric source of carbon which is deemed to not be environmentally sensitive.

In the field of air freshening it is generally preferred to use a fragranced volatile liquid/air freshening liquids comprising several components. These components often possess different volatilities which can lead to emission problems. The effect of fractionation can be particularly pronounced for powered emanation devices using a heater to effect emanation such as a plug-in emanation device or the like.

In such device a build-up phenomenon can occur in which an accumulation of volatile liquid components with the lowest comparative volatilities can occur leading to an undesirable non-uniform emanation profile for the liquid. This phenomenon can produce an olfactory sensation wherein the fragrance character changes over the course of emanation of a quantity of the fragranced volatile liquid such that the 'high notes' of a fragrance are the first to be evaporated when the wicking material is first exposed to the fragranced liquid, and the 'low notes' are evaporated thereafter.

Accordingly, it is an object of the present invention to provide a device that is capable of addressing the abovementioned performance drawbacks and other drawbacks that will be appreciated by a person skilled in the art.

SUMMARY OF INVENTION

According to a first aspect of the present invention there is provided therefore an emanation system comprising and emanation device and a replaceable refill of liquid, wherein the refill comprises:

a sealed reservoir of a liquid containing one or more active materials wherein the active material comprises at least one of: a fragrance; an insecticide; a fungicide; a pesticide; a sanitising material; and/or a pharmaceutical;

a porous wick having a length which extends from the interior of the reservoir to the exterior thereof;

a reservoir seal having at least one aperture through which the porous wick extends; and a hollow liquid conduit housed within the wick having a length substantially identical to the wick; and wherein the device comprises:

an air pump;

a fluid conduit in fluid communication with the air pump such that, in use, air pumped by the pump will flow through the fluid conduit;

a nozzle located at the end of the fluid conduit remote from the air pump;

a ejector constriction provided in the fluid conduit adjacent or substantially adjacent the nozzle;

a liquid conduit engaging member provided adjacent the ejector constriction and in fluid communication with the fluid conduit at one end thereof, and configured at the other end to, in use, engage the hollow liquid conduit in the refill.

According to a second aspect of the present invention there is provided therefore an emanation system comprising and emanation device and a replaceable refill of liquid, wherein the refill comprises:

a sealed reservoir of a liquid containing one or more active materials wherein the active material comprises at least one of: a fragrance; an insecticide; a fungicide; a pesticide; a sanitising material; and/or a pharmaceutical;

a porous wick having a length which extends from the interior of the reservoir to the exterior thereof;

a reservoir seal having at least two apertures, wherein the wick extends through one of the apertures; and a hollow liquid conduit which extends from the interior of the reservoir to engage with one of the apertures;

and wherein the device comprises:

an air pump;

a fluid conduit in fluid communication with the air pump such that, in use, air pumped by the pump will flow through the fluid conduit;

a nozzle located at the end of the fluid conduit remote from the air pump;

a ejector constriction provided in the fluid conduit adjacent or substantially adjacent the nozzle;

a liquid conduit engaging member provided adjacent the ejector constriction and in fluid communication with the fluid conduit at one end thereof, and configured at the other end to, in use, engage the hollow liquid conduit in the refill.

According to a third aspect of the present invention there is provided a refill of liquid, wherein the refill comprises:

a sealed reservoir of a liquid containing one or more active materials wherein the active material comprises at least one of: a fragrance; an insecticide; a fungicide; a pesticide; a sanitising material; and/or a pharmaceutical;

a porous wick having a length which extends from the interior of the reservoir to the exterior thereof;

a reservoir seal having at least one aperture through which the porous wick extends; and a hollow liquid conduit housed within the wick having a length substantially identical to the wick.

According to a fourth aspect of the present invention there is provided a refill of liquid, wherein the refill comprises:

a sealed reservoir of a liquid containing one or more active materials wherein the active material comprises at least one of: a fragrance; an insecticide; a fungicide; a pesticide; a sanitising material; and/or a pharmaceutical;

a porous wick having a length which extends from the interior of the reservoir to the exterior thereof;

a reservoir seal having at least two apertures, wherein the wick extends through one of the apertures; and a hollow liquid conduit which extends from the interior of the reservoir to engage with one of the apertures;

Systems according to either the first of second aspect of the present invention have been found to be particularly advantageous as they are capable of spraying the volatile liquid at a uniform consistency thus avoiding the drawbacks of fractionation and/or build-up phenomena.

Refills according to either the third or fourth aspect of the present invention have been found to be particularly advantageous as they can be use with emanation devices that rely on the wicking and capillary action of the wick to transport the liquid to the exterior of the refill where heat is applied to accelerate the volatilisation of the liquid and can be used with emanation devices as described in the systems of the first and second aspects of the invention.

The liquid conduit is preferably made from a rigid or substantially rigid material such as a metal, alloy or plastics material. A plastics material is generally preferred, suitable plastics materials include the materials used in aerosol diptubes as they are generally compatible with the liquids containing the active material(s).

The hollow liquid conduit in the first aspect of the present invention is provided with length that is substantially identical to the length of the wick, this is advantageous as it permits the manufacture of the wick and conduit to be less expensive as it can be manufactured together and/or cut into desired lengths together.

The hollow liquid conduit in the second aspect of the present invention is preferably provided with length that permits it to extend between the extremity of the reservoir remote to the seal and the seal with the conduit preferably terminating at or adjacent the seal.

The refill may be made from a reservoir that is partially or completely transparent thus allowing a user to monitor the liquid level therein. Preferably the reservoir is made from glass or a substantially rigid plastics material.

The reservoir seal is preferably sized to correspond to the diameter or cross-section of the wick thus securely holding the wick in a fixed position whilst substantially maintaining a liquid seal to substantially or completely prevent the leaking of liquid from the reservoir.

The refill is preferably provided with a removable cap that surrounds the seal and the protruding wick to protect the wick and prevent emanation of the volatile liquid from the wick until emanation of the volatile liquid is required.

The wick is preferably made from a wrapped fibrous material, such as wrapped cellulose or the like.

The wick is preferably sized to extend from a base of reservoir to protrude through the plug or a reservoir seal to extend thereabove.

The device may be provided with refill securing means which are configured to retain the refill in a substantially fixed position relative to the device to ensure the safe operation of the device during use and prevent the likelihood of damage to the liquid conduit.

The air pump is preferably configured to pump air through the fluid conduit within a range of substantially 0.4-1.0 liters/min, and preferably substantially 0.6-0.8 liters/min.

The ejector constriction is preferably provided in the form of a nozzle insert, even more preferably said nozzle insert substantially fills the nozzle and permits the flow of volatile liquid therefrom.

The nozzle insert is preferably configured to extend from or adjacent the nozzle along the interior of the fluid conduit and may be provided at a rearward portion thereof that is remote from the nozzle with a channel. The channel may be inwardly tapered toward a forward portion thereof to, in use, further lower the pressure and increase the speed of air pumped therethrough, forward of the inward taper may be provided a ejector constriction portion. Forward from said ejector constriction portion may be provided an expansion chamber. The liquid conduit engaging member preferably connects to the fluid conduit in the ejector constriction portion to be in fluid communication with the fluid conduit and/or the nozzle insert such that, in use, the decrease in pressure at the connection draws liquid up the liquid conduit n the refill into the liquid conduit engaging member and into the fluid conduit and/or nozzle insert before being carried by the pumped air flow out of the nozzle or nozzle insert into the environment surrounding the device.

Alternatively the ejector constriction can be formed integrally with the fluid conduit adjacent the nozzle. As a further alternative the ejector constriction can be formed integrally with the nozzle.

The nozzle or nozzle insert may be provided with one or more break-up bars and/or swirl chambers in order to improve the mechanical break up of the volatile liquid being sprayed therefrom in use.

The device is preferably provided with a controller that is configured to control the air pump to control the spraying of volatile liquid from the device. Preferably the controller is provided with a timer to permit the controller to instruct the pump to operate for periods defined by the controller. The device may be provided with user input means to allow a user to instruct the controller how long to spray for and/or how often to spray for and/or the spray rate of the device.

The device may be provided with a sensor means which is connected to the controller wherein said sensor means is configured to detect a characteristic in the environment surrounding the device. The controller would preferably be operative to analyse an input from the sensor means and control the air pump to spray a determined amount of volatile liquid.

Preferably the sensor means is provided by at least one motion sensor means and/or at least one odour sensor means.

The motion sensor means may be provided in the form of at least one of: an infrared (IR) sensor; a laser sensor; and a sound sensor. The IR sensor, which is preferably a passive IR sensor, may be operable to detect radiation in the infrared spectrum, thus be capable of detecting the presence of a person or an animal within the vicinity of the device. The laser sensor may be operable to emit one or more laser beams and be adapted to detect when an object breaks the one or more beams by moving across the beam(s), thus indicating the presence of a person or an animal within the vicinity of the device. The sound sensor may be operable to detect sound within the vicinity of the device and, preferably, once the detected sound exceeds a predefined level this is indicative of movement within the vicinity of the device.

The odour sensor means may be provided by a MOS sensor or the like and may be operable to detect common household odours (and the chemicals which constitute) these malodours. For example: kitchen malodour; bathroom malodour; tobacco smoke; pet odours; mould and/or mildew; body odour; fish; onions; garbage; fragrance from other products (such as detergents, polishes, cleaning products etc). To facilitate such detection the odour sensor means may be operable to detect at least some of the following chemical components: amines and nitrogen compounds; acids and/or sulphur compounds, such as mercaptans, thioacids, thioesters, sulfides, phenols and skatole.

The device of any of the above-mentioned aspects may be provided with an indicator wherein said indicator is operable to indicate to a user what function the device is currently performing. The indicator may be operable to provide a visual indication and/or provide an audible indication.

Preferably the indicator is configured to provide a visual indication by emitting light from one or more light sources, preferably one or more LEDs.

The one or more light sources may be adapted to emit a different colour of light to indicate the current function the device is performing. Additionally or alternatively, the one or more light sources may blink or flash to indicate the current function the device is performing.

Alternatively or additionally, the device may be operable to visually indicate the function currently being performed by the device via a screen. The screen may be an LCD screen that is adapted to provide a message to a user, for instance such messages could include "ON", "DISPENSING", "RESTING", "NORMAL MODE", "DETECTING MODE", "BOOST MODE", "OFF".

The device may be power by mains-supplied electricity and/or be battery powered and/or be powered by solar cells located on the device. Most preferably the device is battery powered however to improve the portability thereof. Indeed battery powered is preferred as the use of such power is consider to be particularly advantageous over typical devices used for emanating volatile liquids from a wicked replaceable refill, such as a mains electrical plug in diffuser, is that the device does not need to be located adjacent an electrical plug socket nor within an acceptable distance of the socket such that there can be a electrical power cord between the device and plug socket, thus providing true portability.

Any of the features described herein may be combined with any of the above aspects in any combination.

BRIEF DESCRIPTION OF THE DRAWINGS

Embodiments of the invention will now be described, by way of example only, with reference to the following drawing in which.

DESCRIPTION OF AN EMBODIMENT

Figure 1:
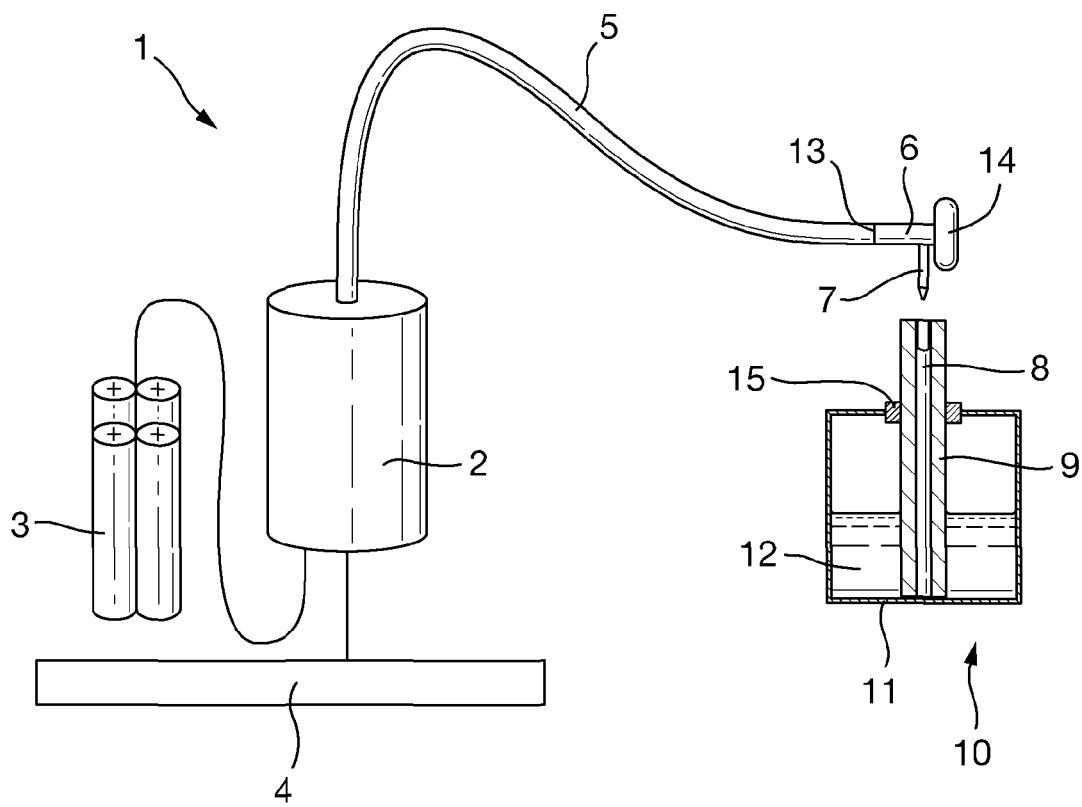
FIG. 1 illustrates an exploded view of the principle components of a device according to the first aspect of the present invention.

FIG. 1 illustrates an exploded view of the principle components of the system according to the first aspect of the present invention. The device 1 consists of an air pump 2 which is powered by batteries 3 and controlled by a controller 4 provided in the form of a PCB with suitable components attached thereto to facilitate control of the air pump 2.

The air pump 2 is shown in fluid communication with a fluid conduit 5 such that air pumped by the pump 5 is pumped into the fluid conduit 6. The pumped air passes along the fluid conduit through a nozzle insert 6 (discussed in greater detail below) and out of a nozzle (not shown). Connected to the fluid conduit 5 around the nozzle insert 6 is a liquid conduit engaging member 7.

The liquid conduit engaging member 7 is made from a rigid or substantially rigid material such as a metal, alloy or plastics material, and is of a generally tubular construction to permit volatile liquid to be transported therein and having a generally tapered end to permit engagement with a hollow liquid conduit 8.

The refill 10 comprises a reservoir 11 that is partially or completely transparent thus allowing a user to monitor the volatile liquid 12 level therein. The reservoir 11 is sealed with a seal 15 having an aperture therethrough, and the aperture is sized to correspond to the diameter or cross-section of the wick 9 to securely hold it in a fixed position whilst substantially maintaining a liquid seal to substantially or completely prevent the leaking of liquid from the reservoir.

Although not shown in detail in FIG. 1, the nozzle insert 6 is configured to be held in place by the nozzle and extend therefrom along the interior of the fluid conduit 5. At a rearward portion 13 of the nozzle insert 6 a channel is provided which may be inwardly tapered toward a forward portion (i.e. toward the nozzle) thereof to, in use, further lower the pressure and increase the speed of air pumped therethrough. Forward of the inward taper may be provided a ejector constriction portion 14 and forward from said ejector constriction portion may be provided an expansion chamber. The liquid conduit 8 connects to the fluid conduit 5 in the ejector constriction 14 portion to be in fluid communication with the fluid conduit 5 and/or the nozzle insert 6 such that, in use, the decrease in pressure at the connection draws liquid up the liquid conduit 8 into the liquid conduit engaging member 7 and further into the fluid conduit 5 and/or nozzle insert 6 before being carried by the pumped air flow out of the nozzle into the environment surrounding the device 1.

Figure 2:
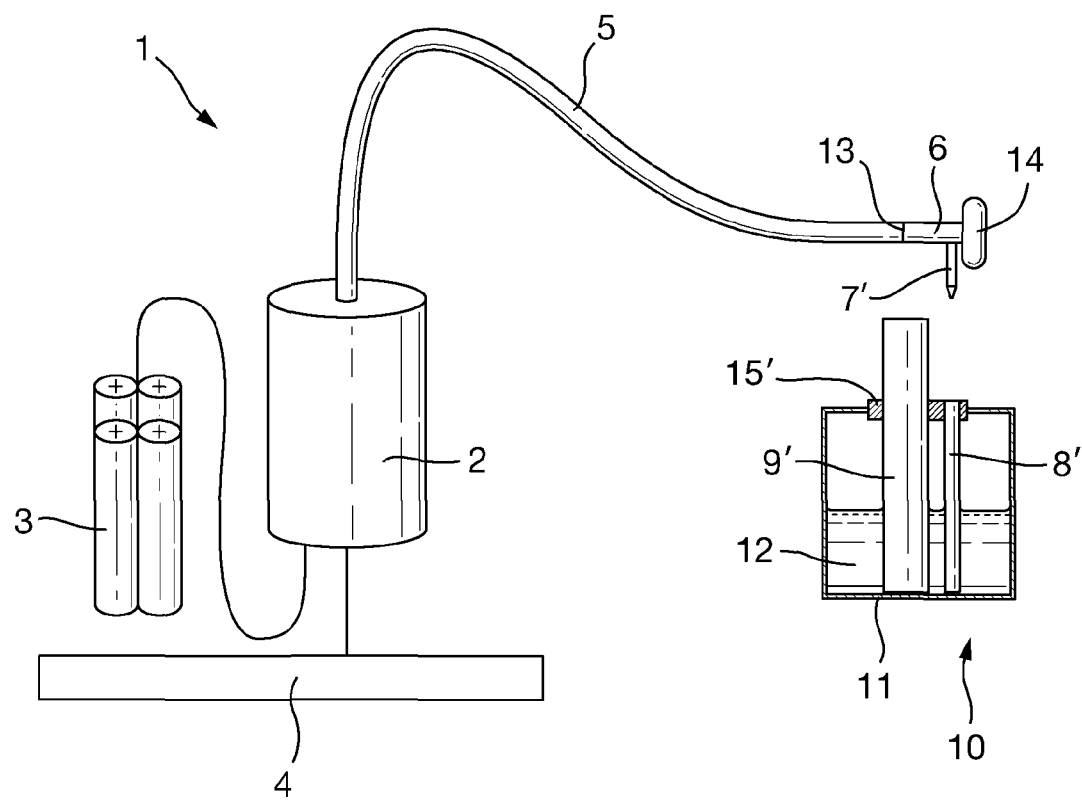
FIG. 2 illustrates an exploded view of the principle components of a device according to the first aspect of the present invention.

FIG. 2 illustrates an exploded view of the principle components of the system according to the second aspect of the present invention. The only difference of note over the system as described with reference to FIG. 1 is that the liquid conduit 7' is held by the seal 15' in a first aperture engagement with the liquid in the reservoir whereas the seal 15' holds the wick 9 in a second aperture. Additionally it can be seen that the conduit 7' terminates adjacent to a top surface of the seal 15' rather than a top surface of the wick 9'.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. An emanation system comprising and emanation device and a replaceable refill of liquid,
    wherein the refill comprises:
        a sealed reservoir of a liquid containing one or more active materials wherein the active material comprises at least one of: a fragrance; an insecticide; a fungicide; a pesticide; a sanitising material; and/or a pharmaceutical;
        a porous wick having a length which extends from the interior of the reservoir to the exterior thereof;
        a reservoir seal having at least one aperture through which the porous wick extends; and a hollow liquid conduit housed within the wick having a length substantially identical to the wick;
    and wherein the device comprises:
        an air pump;
        a fluid conduit in fluid communication with the air pump such that, in use, air pumped by the pump will flow through the fluid conduit;
        a nozzle located at the end of the fluid conduit remote from the air pump;
        a ejector constriction provided in the fluid conduit adjacent or substantially adjacent the nozzle; a liquid conduit engaging member provided adjacent the ejector constriction and in fluid communication with the fluid conduit at one end thereof, and configured at the other end to, in use, engage the hollow liquid conduit in the refill.

2. An emanation system according to claim 1, wherein the liquid conduit is made from a rigid or substantially rigid material.

3. An emanation system according to claim 1, wherein the refill is made from a reservoir that is partially or completely transparent.

4. An emanation system according to claim 1, wherein the reservoir seal is sized to correspond to the diameter or cross-section of the wick thus securely holding the wick in a fixed position whilst substantially maintaining a liquid seal to substantially or completely prevent the leaking of liquid from the reservoir.

5. An emanation system according to claim 1, wherein the air pump is configured to pump air through the fluid conduit within a range of substantially 0.4-1.0 liters/min, and preferably substantially 0.6-0.8 liters/min.

6. An emanation system according to claim 1, wherein the ejector constriction is provided in the form of a nozzle insert and said nozzle insert is configured to extend from or adjacent the nozzle along the interior of the fluid conduit and is provided at a rearward portion thereof that is remote from the nozzle with a channel, and wherein said channel is inwardly tapered toward a forward portion thereof to, in use, further lower the pressure and increase the speed of air pumped therethrough, forward of the inward taper is provided a ejector constriction portion, and wherein forward from said ejector constriction portion is provided an expansion chamber, such that, in use, the liquid conduit engaging member connects to the fluid conduit in the ejector constriction portion to be in fluid communication with the fluid conduit and/or the nozzle insert wherein the decrease in pressure at the connection draws liquid up the liquid conduit in the refill into the liquid conduit engaging member and into the fluid conduit and/or nozzle insert before being carried by the pumped air flow out of the nozzle or nozzle insert into the environment surrounding the device.

7. An emanation system comprising and emanation device and a replaceable refill of liquid,
    wherein the refill comprises:
        a sealed reservoir of a liquid containing one or more active materials wherein the active material comprises at least one of: a fragrance; an insecticide; a fungicide; a pesticide; a sanitising material; and/or a pharmaceutical;
        a porous wick having a length which extends from the interior of the reservoir to the exterior thereof;
        a reservoir seal having at least two apertures, wherein the wick extends through one of the apertures; and
        a hollow liquid conduit which extends from the interior of the reservoir to engage with one of the apertures;
    and wherein the device comprises:
        an air pump;
        a fluid conduit in fluid communication with the air pump such that, in use, air pumped by the pump will flow through the fluid conduit;
        a nozzle located at the end of the fluid conduit remote from the air pump;
        a ejector constriction provided in the fluid conduit adjacent or substantially adjacent the nozzle; a liquid conduit engaging member provided adjacent the ejector constriction and in fluid communication with the fluid conduit at one end thereof, and configured at the other end to, in use, engage the hollow liquid conduit in the refill.

8. An emanation system according to claim 7, wherein the hollow liquid conduit is provided with length that permits it to extend between the extremity of the reservoir remote to the seal and the seal wherein the conduit terminates at or adjacent the seal.

9. An emanation system according to claim 7, wherein the liquid conduit is made from a rigid or substantially rigid material.

10. An emanation system according to claim 7, wherein the refill is made from a reservoir that is partially or completely transparent.

11. An emanation system according to claim 7, wherein the reservoir seal is sized to correspond to the diameter or cross-section of the wick thus securely holding the wick in a fixed position whilst substantially maintaining a liquid seal to substantially or completely prevent the leaking of liquid from the reservoir.

12. An emanation system according to claim 7, wherein the air pump is configured to pump air through the fluid conduit within a range of substantially 0.4-1.0 liters/min, and preferably substantially 0.6-0.8 liters/min.

13. An emanation system according to claim 7, wherein the ejector constriction is provided in the form of a nozzle insert and said nozzle insert is configured to extend from or adjacent the nozzle along the interior of the fluid conduit and is provided at a rearward portion thereof that is remote from the nozzle with a channel, and wherein said channel is inwardly tapered toward a forward portion thereof to, in use, further lower the pressure and increase the speed of air pumped therethrough, forward of the inward taper is provided a ejector constriction portion, and wherein forward from said ejector constriction portion is provided an expansion chamber, such that, in use, the liquid conduit engaging member connects to the fluid conduit in the ejector constriction portion to be in fluid communication with the fluid conduit and/or the nozzle insert wherein the decrease in pressure at the connection draws liquid up the liquid conduit in the refill into the liquid conduit engaging member and into the fluid conduit and/or nozzle insert before being carried by the pumped air flow out of the nozzle or nozzle insert into the environment surrounding the device.

14. A refill of liquid, wherein the refill comprises:
- a sealed reservoir of a liquid containing one or more active materials wherein the active material comprises at least one of: a fragrance; an insecticide; a fungicide; a pesticide; a sanitising material; and/or a pharmaceutical;
- a porous wick having a length which extends from the interior of the reservoir to the exterior thereof;
- a reservoir seal having at least one aperture through which the porous wick extends; and
- a hollow liquid conduit housed within the wick having a length substantially identical to the wick.

15. A refill of liquid according to claim 14, wherein the liquid conduit is made from a rigid or substantially rigid material such as a metal, alloy or plastics material.

16. A refill of liquid, wherein the refill comprises:
- a sealed reservoir of a liquid containing one or more active materials wherein the active material comprises at least one of: a fragrance; an insecticide; a fungicide; a pesticide; a sanitising material; and/or a pharmaceutical;
- a porous wick having a length which extends from the interior of the reservoir to the exterior thereof;
- a reservoir seal having at least two apertures, wherein the wick extends through one of the apertures; and
- a hollow liquid conduit which extends from the interior of the reservoir to engage with one of the apertures.

* * * * *